(12) United States Patent
Soler et al.

(10) Patent No.: US 11,426,555 B2
(45) Date of Patent: *Aug. 30, 2022

(54) LUMINAIRES, SYSTEMS AND METHODS FOR PROVIDING SPECTRALLY AND SPATIALLY MODULATED ILLUMINATION

(71) Applicant: Biological Innovation and Optimization Systems, LLC, Carlsbad, CA (US)

(72) Inventors: Robert Soler, San Marcos, CA (US); Eric Thosteson, Satellite Beach, FL (US)

(73) Assignee: Biological Innovation and Optimization Systems, LLC, Carlsbad, CA (US)

( * ) Notice: Subject to any disclaimer, the term of this patent is extended or adjusted under 35 U.S.C. 154(b) by 265 days.

This patent is subject to a terminal disclaimer.

(21) Appl. No.: 16/816,932

(22) Filed: Mar. 12, 2020

(65) Prior Publication Data

US 2020/0214101 A1    Jul. 2, 2020

Related U.S. Application Data

(63) Continuation of application No. 15/609,294, filed on May 31, 2017, now Pat. No. 10,595,376.
(Continued)

(51) Int. Cl.
*A61M 21/02* (2006.01)
*H05B 45/20* (2020.01)
(Continued)

(52) U.S. Cl.
CPC .......... *A61M 21/02* (2013.01); *A61N 5/0618* (2013.01); *H05B 45/20* (2020.01);
(Continued)

(58) Field of Classification Search
CPC ...... A61M 21/00–02; A61N 2005/0651–0654; A61N 2005/0663;
(Continued)

(56) References Cited

U.S. PATENT DOCUMENTS 3,869,605 A    3/1975 Davis
3,931,695 A    1/1976 Widmayer
(Continued)

OTHER PUBLICATIONS

Author L E Fred Schubert, Title: Light-Emitting Diodes, Date: Dec. 2006 pp. 1-434.
(Continued)

*Primary Examiner* — Thaddeus B Cox
(74) *Attorney, Agent, or Firm* — MLO, a professional corp.

(57) ABSTRACT

Embodiments include a lighting device that includes a first illumination source comprising a light-emitting diode (LED) of a first color that generates a first light output with a first melanopic ratio of 0.4 to 1.2, and a second illumination source comprising an LED of a second color that generates a second light output with a second melanopic ratio that is less than the first melanopic ratio. The lighting device also includes a light distribution unit for directing and distributing illumination generated by the first and second illumination sources, where at least one of the first illumination source and the second illumination source is affixed to the light distribution unit, and where the first and second illumination sources are oriented relative to one another such that their respective light outputs are directed in different directions.

15 Claims, 3 Drawing Sheets

Related U.S. Application Data

(60) Provisional application No. 62/434,791, filed on Dec. 15, 2016, provisional application No. 62/408,635, filed on Oct. 14, 2016, provisional application No. 62/393,714, filed on Sep. 13, 2016.

(51) Int. Cl.

| | | |
|---|---|---|
| *A61N 5/06* | (2006.01) | |
| *F21V 1/00* | (2006.01) | |
| *F21Y 115/10* | (2016.01) | |
| *F21S 6/00* | (2006.01) | |
| *F21Y 113/13* | (2016.01) | |
| *A61M 21/00* | (2006.01) | |
| *H05B 47/16* | (2020.01) | |
| *H05B 47/19* | (2020.01) | |

(52) U.S. Cl.
CPC .............. *A61M 2021/0027* (2013.01); *A61M 2021/0044* (2013.01); *A61M 2205/3368* (2013.01); *A61M 2205/3375* (2013.01); *A61M 2205/587* (2013.01); *A61N 2005/0651* (2013.01); *A61N 2005/0663* (2013.01); *F21S 6/003* (2013.01); *F21V 1/00* (2013.01); *F21Y 2113/13* (2016.08); *F21Y 2115/10* (2016.08); *H05B 47/16* (2020.01); *H05B 47/19* (2020.01)

(58) Field of Classification Search
CPC ........... H05B 45/00–28; F21V 1/00–26; F21S 6/00–008; F21S 10/02–026; F21Y 2113/10–13; F21Y 2115/10–15
See application file for complete search history.

(56) References Cited

U.S. PATENT DOCUMENTS

| | | | |
|---|---|---|---|
| 4,768,390 A | 9/1988 | Baker et al. | |
| 5,012,609 A | 5/1991 | Ignatius et al. | |
| 5,253,302 A | 10/1993 | Massen | |
| 5,299,383 A | 4/1994 | Takakura et al. | |
| 5,606,821 A | 3/1997 | Sadjadi et al. | |
| 5,813,753 A | 9/1998 | Vriens et al. | |
| 5,851,063 A | 12/1998 | Doughty et al. | |
| 5,959,316 A | 9/1999 | Lowery | |
| 6,294,800 B1 | 9/2001 | Duggal et al. | |
| 6,357,889 B1 | 3/2002 | Duggal et al. | |
| 6,441,558 B1 | 8/2002 | Muthu et al. | |
| 6,459,919 B1 | 10/2002 | Lys et al. | |
| 6,538,371 B1 | 3/2003 | Duggal et al. | |
| 6,552,495 B1 | 4/2003 | Chang | |
| 6,554,439 B1 | 4/2003 | Teicher et al. | |
| 6,554,450 B2 | 4/2003 | Fang et al. | |
| 6,577,080 B2 | 6/2003 | Lys et al. | |
| 6,586,882 B1 | 7/2003 | Harbers | |
| 6,636,003 B2 | 10/2003 | Rahm et al. | |
| 6,641,283 B1 | 11/2003 | Bohler | |
| 6,680,200 B2 | 1/2004 | Everett | |
| 6,685,852 B2 | 2/2004 | Setlur et al. | |
| 6,734,465 B1 | 5/2004 | Taskar et al. | |
| 6,880,291 B2 | 4/2005 | Raun et al. | |
| 6,914,265 B2 | 7/2005 | Bawendi et al. | |
| 6,921,182 B2 | 7/2005 | Anderson et al. | |
| 6,936,857 B2 | 8/2005 | Doxsee et al. | |
| 6,967,116 B2 | 11/2005 | Negley | |
| 7,005,679 B2 | 2/2006 | Tarsa et al. | |
| 7,008,559 B2 | 3/2006 | Chen | |
| 7,015,636 B2 | 3/2006 | Bolta | |
| 7,034,934 B2 | 4/2006 | Manning | |
| 7,052,157 B1 | 5/2006 | Lau | |
| 7,058,197 B1 | 6/2006 | McGuire et al. | |
| 7,125,143 B2 | 10/2006 | Hacker | |
| 7,135,664 B2 | 11/2006 | Vomsand et al. | |
| 7,215,074 B2 | 5/2007 | Shimizu et al. | |
| 7,222,220 B2 | 5/2007 | Cypher et al. | |
| 7,234,844 B2 | 6/2007 | Bolta et al. | |
| 7,250,715 B2 | 7/2007 | Mueller et al. | |
| 7,255,457 B2 | 8/2007 | Ducharme et al. | |
| 7,256,557 B2 | 8/2007 | Lim et al. | |
| 7,264,527 B2 | 9/2007 | Bawendi et al. | |
| 7,319,293 B2 | 1/2008 | Maxik | |
| 7,324,076 B2 | 1/2008 | Lee et al. | |
| 7,365,485 B2 | 4/2008 | Fukasawa et al. | |
| 7,382,091 B2 | 6/2008 | Chen et al. | |
| 7,387,405 B2 | 6/2008 | Ducharme et al. | |
| 7,520,607 B2 | 4/2009 | Casper et al. | |
| 7,573,210 B2 | 8/2009 | Ashdown et al. | |
| 7,598,686 B2 | 10/2009 | Lys et al. | |
| 7,598,961 B2 | 10/2009 | Higgins | |
| 7,678,140 B2 | 3/2010 | Brainard et al. | |
| 7,679,281 B2 | 3/2010 | Kim et al. | |
| 7,684,007 B2 | 3/2010 | Hull et al. | |
| 7,703,943 B2 | 4/2010 | Li et al. | |
| 7,728,846 B2 | 6/2010 | Higgins et al. | |
| 7,748,845 B2 | 7/2010 | Casper et al. | |
| 7,828,453 B2 | 11/2010 | Tran et al. | |
| 7,845,823 B2 | 12/2010 | Mueller et al. | |
| 7,972,030 B2 | 7/2011 | Li | |
| 7,984,989 B2 | 7/2011 | Gruber | |
| 8,038,314 B2 | 10/2011 | Ladewig | |
| 8,115,419 B2 | 2/2012 | Given et al. | |
| 8,192,047 B2 | 6/2012 | Bailey et al. | |
| 8,207,676 B2 | 6/2012 | Hilgers | |
| 8,253,336 B2 | 8/2012 | Maxik et al. | |
| 8,256,921 B2 | 9/2012 | Crookham et al. | |
| 8,297,783 B2 | 10/2012 | Kim | |
| 8,324,808 B2 | 12/2012 | Maxik et al. | |
| 8,324,823 B2 | 12/2012 | Choi et al. | |
| 8,362,684 B2 | 1/2013 | Bawendi et al. | |
| 8,378,574 B2 | 2/2013 | Schlangen et al. | |
| 8,401,231 B2 | 3/2013 | Maxik et al. | |
| 8,410,725 B2 | 4/2013 | Jacobs et al. | |
| 8,441,210 B2 | 5/2013 | Shteynberg et al. | |
| 8,446,095 B2 | 5/2013 | Maxik et al. | |
| 8,513,875 B2 | 8/2013 | Ven et al. | |
| 8,547,391 B2 | 10/2013 | Maxik et al. | |
| 8,643,276 B2 | 2/2014 | Maxik et al. | |
| 8,680,457 B2 | 3/2014 | Maxik et al. | |
| 8,686,641 B2 | 4/2014 | Maxik et al. | |
| 8,743,023 B2 | 6/2014 | Maxik et al. | |
| 8,754,832 B2 | 6/2014 | Maxik et al. | |
| 8,901,850 B2 | 12/2014 | Maxik et al. | |
| 8,941,329 B2 | 1/2015 | Maxik et al. | |
| 9,024,536 B2 | 5/2015 | Maxik et al. | |
| 9,030,103 B2 | 5/2015 | Pickard | |
| 9,036,244 B2 | 5/2015 | Maxik et al. | |
| 9,039,746 B2 | 5/2015 | Ven et al. | |
| 9,052,067 B2 | 6/2015 | Ven et al. | |
| 9,055,644 B2 | 6/2015 | Nagashima et al. | |
| 9,127,818 B2 | 9/2015 | Maxik et al. | |
| 9,131,573 B2 | 9/2015 | Maxik et al. | |
| 9,137,874 B2 | 9/2015 | Maxik et al. | |
| 9,173,269 B2 | 10/2015 | Maxik et al. | |
| 9,174,067 B2 | 11/2015 | Maxik et al. | |
| 9,220,202 B2 | 12/2015 | Maxik et al. | |
| 9,265,968 B2 | 2/2016 | Maxik et al. | |
| 9,289,574 B2 | 3/2016 | Maxik et al. | |
| 9,322,516 B2 | 4/2016 | Boomgaarden et al. | |
| 9,326,454 B2 | 5/2016 | Suzuki | |
| 9,353,916 B2 | 5/2016 | Maxik et al. | |
| 9,441,793 B2 | 9/2016 | Ven et al. | |
| 9,872,359 B2 | 1/2018 | Adler | |
| 2001/0002049 A1 | 5/2001 | Reeh et al. | |
| 2001/0047618 A1 | 12/2001 | Fang et al. | |
| 2002/0026659 A1 | 2/2002 | Blowers et al. | |
| 2003/0005626 A1 | 1/2003 | Yoneda et al. | |
| 2003/0009933 A1 | 1/2003 | Yoneda et al. | |
| 2004/0052076 A1 | 3/2004 | Mueller et al. | |
| 2004/0105261 A1 | 6/2004 | Ducharme et al. | |
| 2004/0109302 A1 | 6/2004 | Yoneda et al. | |
| 2004/0217364 A1 | 11/2004 | Tarsa et al. | |
| 2004/0218387 A1 | 11/2004 | Gerlach | |
| 2004/0259363 A1 | 12/2004 | Bawendi et al. | |
| 2004/0264193 A1 | 12/2004 | Okumura | |

(56) References Cited

U.S. PATENT DOCUMENTS

| | | |
|---|---|---|
| 2005/0030744 A1 | 2/2005 | Ducharme et al. |
| 2005/0267213 A1 | 12/2005 | Gold et al. |
| 2005/0281027 A1 | 12/2005 | Capen et al. |
| 2006/0002110 A1 | 1/2006 | Dowling et al. |
| 2006/0053691 A1 | 3/2006 | Harwood et al. |
| 2006/0104058 A1 | 5/2006 | Chemel et al. |
| 2006/0105482 A1 | 5/2006 | Alferink et al. |
| 2006/0138435 A1 | 6/2006 | Tarsa et al. |
| 2006/0152140 A1 | 7/2006 | Brandes |
| 2006/0152172 A9 | 7/2006 | Mueller et al. |
| 2006/0164005 A1 | 7/2006 | Sun |
| 2006/0181192 A1 | 8/2006 | Radkov et al. |
| 2007/0058368 A1 | 3/2007 | Partee et al. |
| 2007/0170447 A1 | 7/2007 | Negley et al. |
| 2007/0276606 A1 | 11/2007 | Radkov et al. |
| 2007/0289207 A1 | 12/2007 | May et al. |
| 2008/0119912 A1 | 5/2008 | Hayes |
| 2008/0302004 A1 | 12/2008 | Lin |
| 2009/0199470 A1 | 8/2009 | Capen et al. |
| 2009/0288340 A1 | 11/2009 | Hess |
| 2010/0020536 A1 | 1/2010 | Bafetti et al. |
| 2010/0076620 A1 | 3/2010 | Loebl et al. |
| 2010/0121420 A1 | 5/2010 | Fiset et al. |
| 2010/0244735 A1 | 9/2010 | Buelow, II |
| 2010/0244740 A1 | 9/2010 | Alpert et al. |
| 2010/0287830 A1 | 11/2010 | Chen et al. |
| 2011/0115385 A1 | 5/2011 | Waumans et al. |
| 2011/0162101 A1 | 6/2011 | Cahoon et al. |
| 2011/0205738 A1 | 8/2011 | Peifer et al. |
| 2011/0209400 A1 | 9/2011 | Rooymans |
| 2011/0242453 A1 | 10/2011 | Ven et al. |
| 2012/0003728 A1 | 1/2012 | Lanoue et al. |
| 2012/0206050 A1 | 8/2012 | Spero |
| 2012/0218750 A1 | 8/2012 | Klase et al. |
| 2012/0281403 A1 | 11/2012 | Kang |
| 2013/0021792 A1 | 1/2013 | Snell et al. |
| 2013/0201717 A1 | 8/2013 | Holman |
| 2013/0255150 A1 | 10/2013 | Karpinski et al. |
| 2013/0278148 A1 | 10/2013 | Maxik et al. |
| 2013/0278172 A1 | 10/2013 | Maxik et al. |
| 2013/0293148 A1 | 11/2013 | Holland et al. |
| 2013/0320862 A1 | 12/2013 | Campbell et al. |
| 2014/0015438 A1 | 1/2014 | Maxik et al. |
| 2014/0049191 A1 | 2/2014 | Maxik et al. |
| 2014/0049192 A1 | 2/2014 | Maxik et al. |
| 2014/0185281 A1 | 7/2014 | Lee et al. |
| 2014/0215911 A1 | 8/2014 | Suzuki |
| 2014/0232288 A1 | 8/2014 | Brandes et al. |
| 2014/0259905 A1 | 9/2014 | Ovadya et al. |
| 2014/0330406 A1 | 11/2014 | Faris |
| 2015/0128489 A1 | 5/2015 | Yamada et al. |
| 2015/0223402 A1 | 8/2015 | Krijn et al. |
| 2015/0241029 A1 | 8/2015 | York et al. |
| 2016/0037730 A1 | 2/2016 | Whittingham |
| 2016/0047538 A1 | 2/2016 | Peck et al. |
| 2016/0143109 A1 | 5/2016 | Lal et al. |
| 2017/0068033 A1 | 3/2017 | Kennedy |
| 2017/0231055 A1 | 8/2017 | Yadav et al. |
| 2017/0299167 A1 | 10/2017 | Cai |
| 2017/0354000 A1 | 12/2017 | Gordin et al. |
| 2018/0043130 A1 | 2/2018 | Moore-Ede et al. |
| 2018/0056027 A1 | 3/2018 | Peeters et al. |
| 2018/0235041 A1* | 8/2018 | Trouwborst ........... H05B 45/22 |

OTHER PUBLICATIONS

Final Office Action dated Mar. 4, 2020 for U.S. Appl. No. 16/543,921.
Non-Final Office Action dated Jan. 8, 2019 for U.S. Appl. No. 15/833,023.
Notice of Allowance dated Nov. 26, 2019 for U.S. Appl. No. 15/609,294.
Office Action dated Mar. 11, 2019 for U.S. Appl. No. 15/875,143.
Office Action dated Nov. 15, 2018 for U.S. Appl. No. 15/875,143.
Office Action dated Oct. 21, 2019 for U.S. Appl. No. 16/543,921.
Office Action dated Oct. 23, 2019 for U.S. Appl. No. 15/609,294.
Prattis, "LED Wavelength vs. LED Colour,", Jul. 16, 2015, DESIGNSPARK, https://www.rs-online.com/designspark/led-wavelength-vs-led-colour.

* cited by examiner

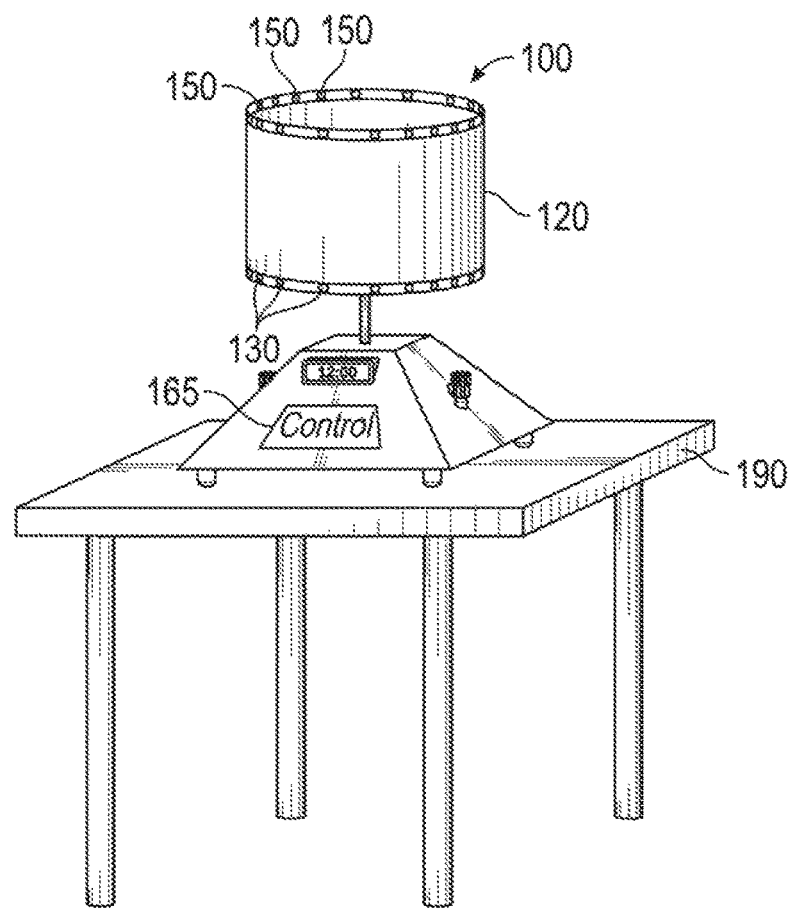
FIG. 1C
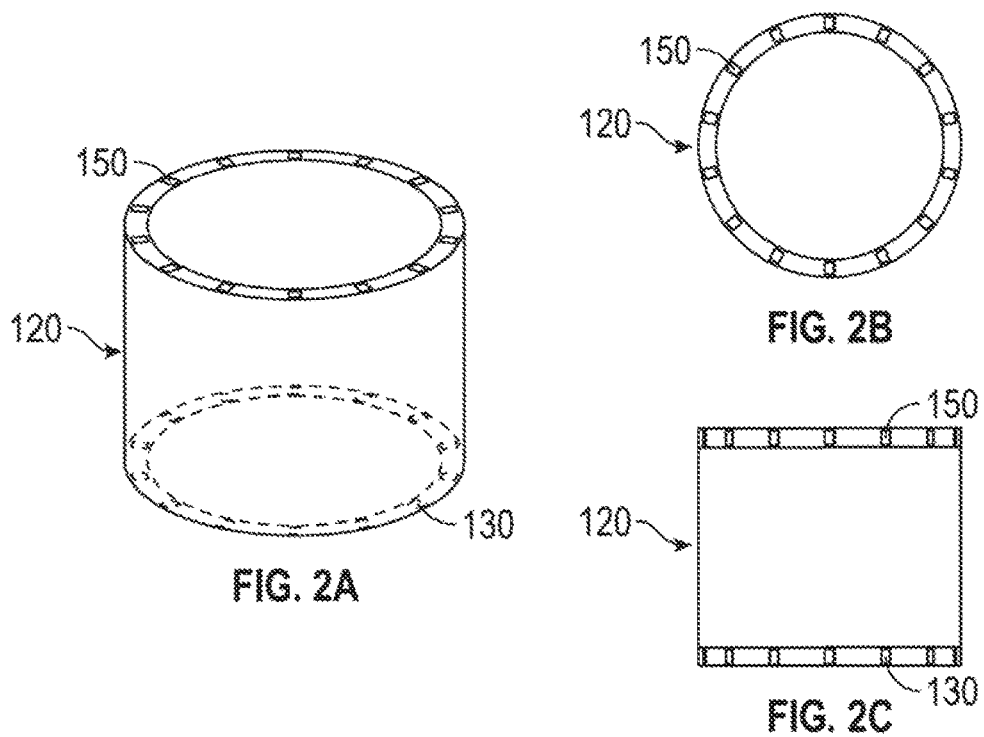
FIG. 2A
FIG. 2B
FIG. 2C

LUMINAIRES, SYSTEMS AND METHODS FOR PROVIDING SPECTRALLY AND SPATIALLY MODULATED ILLUMINATION

RELATED APPLICATIONS

This application is a continuation of U.S. patent application Ser. No. 15/609,294, filed on May 31, 2017, now U.S. Pat. No. 10,595,376, and entitled "Systems and Methods for Controlling the Spectral Content of LED Lighting Devices"; which claims priority to and the benefit of U.S. Provisional Application No. 62/393,714, filed Sep. 13, 2016, U.S. Provisional Application No. 62/408,635, filed Oct. 14, 2016, and U.S. Provisional Application No. 62/434,791, filed Dec. 15, 2016. The contents of these applications are incorporated herein in their entirety. This application is related to U.S. patent application Ser. No. 15/264,197 filed Sep. 13, 2016, now U.S. Pat. No. 9,788,387, and Ser. No. 15/364,533 filed Nov. 30, 2016, now U.S. Pat. No. 9,844,116; both of the aforementioned applications are incorporated herein in their entireties.

Except to the extent that any of the disclosure in the referenced patents conflicts with the disclosure herein, the following US patents, which include inter alia disclosure pertaining to light emitting diode (LED) luminaires and light engines, light distribution units including edge lit units, and LED driving and switching methods are incorporated herein by reference in their entireties: US Patent and Publication Numbers U.S. Pat. Nos. 9,310,545, 9,495,892, 9,541,695, 20100283072 and 20170068033.

FIELD OF THE INVENTION

Embodiments of the invention relate to lighting fixtures, systems and methods for providing spectrally and spatially adjustable high efficacy illumination and that may be used to optimally effect or coordinate with human circadian rhythms.

BRIEF BACKGROUND

Light emitting diode (LED) technology is a maturing technology that continues to show improvements in efficiency, customability and cost reduction. LED technology is rapidly being deployed in a host of industries and markets including general lighting for homes, offices, and transportation, solid state display lighting such as in LCDs, aviation, agricultural, medical, and other fields of application. The increased energy efficiency of LED technology compared with other lighting solutions coupled with the reduction of costs of LED themselves are increasing the number of LED applications and rate of adoptions across industries. While LED technology promises greater reliability, longer lifetimes and greater efficiencies than other lighting technologies, the ability to mix and independently drive different color LEDs to produce customized and dynamic light output makes LED technology and solid state lighting (SSL) in general robust platforms to meet the demands of a variety of market needs and opens the door to many new applications of these lighting technologies. The ability to tailor and tune the output spectra of LED fixtures and dynamically switch individual LEDs "on-the-fly", for example in response to an environmental cue, dramatically opens up the application space of solid state lighting.

As is well known in the art, LED luminaires generally comprise one or more individual LEDs dies or packages mounted on a circuit board. The LEDs may be electrically connected together on a single channel or be distributed and electrically driven across multiple independent channels. The LEDs are typically powered by current from an associated LED driver or power supply. Examples of these power supply drivers include AC/DC and DC/DC switched mode power supplies (SMPS). Examples of LED power drivers include power supplies designed to supply constant current to the LED string in order to maintain a consistent and steady light output from the LEDs. LEDs may also be powered by an AC power source. Direct AC power typically undergoes rectification and other power conditioning prior to being deliver to the LEDs. LED luminaires may also comprise an optic or diffuser, a heat sink and other structural components.

Although LEDs may be combined in such a way to deliver a wide variety of specific color outputs, LED luminaires for general lighting typically are designed to produce white light. Light perceived as white or near-white may be generated by a combination of red, green, and blue (RGB) LEDs. Output color of such a device may be altered by color mixing, for instance varying the amount of illumination produced by each of the respective color LEDs by adjusting the supply of current to each of the red, green, and blue LEDs. Another method for generating white or near-white light is by using a lumiphor such as a phosphor in conjunction with a blue "pump" LED. Still another approach for producing white light is to stimulate phosphors or dyes of multiple colors with an LED source. Many other approaches can also be taken.

Melanopsin is a type of photopigment belonging to a larger family of light-sensitive retinal proteins called opsins, and is found in intrinsically photosensitive retinal ganglion cells (ipRGCs) of humans and other mammals. Melanopsin plays an important non-image-forming role in the photoentrainment of circadian rhythms as well as potentially many other physiologic functions. Stimulation of melanopsin-containing ipRGCs contributes to various reflexive responses of the brain and body to the presence of light. Melanopsin photoreceptors are sensitive to a range of wavelengths and reach peak light absorption at wavelengths around 480-500 (or 490) nanometers (nm). Melanopic light, that is light corresponding to the melanopsin action spectrum, including particularly the wavelengths in the 480-500 nm region is important for non-visual stimuli including physiological and neuroligcal effects such as pupillary light reflex and circadian entrainment and/or disruption. Time coordinated exposure, including over-exposure and under-exposure to melanopic light can be used to entrain and facilitate healthy circadian rhythms in humans and other mammals. When used herein, melanopic light is meant to generally refer to light that stimulates melanopsin and or that may have an effect on human circadian rhythms. When used herein, unless otherwise specified, "melanopic light" is not restricted to a particular or narrow band of wavelengths but rather is meant to mean light that corresponds to or is contained within range of wavelengths that correspond to the that melanopsin action spectrum.

Circadian related photoreceptors are in macular and peripheral vision nearest to the fovea. Melanopsin related photoreceptors are most sensitive in the lower hemisphere of the retina. Selective stimulation of these photoreceptors is possible by directing illumination, and specifically melanopic light, towards or away from the region of the retina where melanopic photoreceptors are most concentrated or most sensitive or responsive. If the desire is to optimally stimulate these photoreceptors, then a light source that produces high biological light (i.e., melanopic light) in this region would be a good solution. Equivalent Melanopic Lux (EML) is a metric for measuring the biological effects of light on humans. EML as a metric is weighted to the ipRGCs response to light and translates how much the spectrum of a light source stimulates ipRGCs and affects the circadian system. Melanopic ratio is the ratio of melanopic lux to photopic lux for a given light source.

The variation of the intensity of light output has a relatively straightforward and understandable effect, namely, higher or lower light intensities incident on the human visual system provide greater or lesser biological stimulation respectively (e.g., with respect to circadian rhythms), the combination of both color variation (e.g., via spectral tuning) and intensity variation can create complementary and in some cases synergistic biological effects. However, spatial distribution is a factor that adds a great deal of complexity and potential cost. Scientific studies have shown that light above the horizon has high biological significance compared with light coming from below the horizon. One consequence of this finding is that illumination emanating (e.g., reflecting) from vertical surfaces (e.g., upper portions of walls and ceilings) has a higher biological significance compared to lower horizontal surfaces (e.g., desktops and tabletops). This differential in biological effect is due at least in part to the fact that there is a greater concentration of melanopsin receptors (ipRGCs) in the lower hemisphere of the human retina than in the upper hemisphere. Thus, the biological effect of light impacting the lower hemisphere of the retina may be greater than the biological effect of the same light incident on the upper hemisphere. This provides an opportunity to further target and optimize biological effects using lighting via spatial distribution and/or spatial modulation of illumination systems, for example by creating layers of light that illuminate different surfaces at different times of day (for example, high vertical illumination during biological daytime, and low vertical illumination during biological night time).

BRIEF SUMMARY

Embodiments of the invention include a lighting device operable to deliver specific spectral and spatial illumination comprising a base, a light distribution unit secured to and above said base wherein the light distribution unit is operable to guide, reflect or transmit light, and a first illumination source comprising an LED of a first color temperature affixed or proximate to a lower portion of said light distribution unit and wherein said LED of the first color temperature is oriented to emit light in a generally upward direction away from said base. These embodiments also include a second illumination source comprising an LED of a second color temperature affixed or proximate to an upper portion of said light distribution unit and wherein the LED of the second color temperature is oriented to emit light in a generally a downward direction toward said base, and an electrical power driver for driving said LEDs to illumination wherein when both LEDS are powered to illumination the resulting illumination in the upward direction away from said base comprises predominantly light of said first color temperature and the resulting illumination in the downward direction toward said base comprises predominantly light of said second color temperature.

In some embodiments, the LED of the first color temperature is rich in melanopic light and the LED of the second color temperature is depleted in melanopic light. In some embodiments, the lighting device is operable to generate high efficacy white light task lighting (direct lighting) and indirect lighting with a comparatively higher equivalent melanopic lux. In some embodiments, a lighting device generates indirect lighting with a relatively high equivalent melanopic lux (EML) and direct lighting with a relatively low equivalent melanopic flux. In some embodiments, a lighting device comprises a first light source of high melanopic ratio and a second light source with low melanopic ratio. In some embodiments a lighting device provides indirect lighting with a melanopic ratio of greater than 0.8 and direct lighting with a melanopic ratio of less than 0.8. Some embodiments of the invention include a lighting device that generates task lighting that is low in melanopic light and generates indirect lighting that is high in melanopic light. In some embodiments, the light distribution unit is comprised of transparent or translucent material and may be composed of acrylic or similar material.

Some embodiments of the invention include a lighting device that comprises a dimmer control wherein the intensity light output of the LED of a first color temperature and the LED of a second color temperature may be independently varied and controlled. In some embodiments of the lighting device, the light distribution unit is adjustable and provides for the varying of the spatial direction, orientation and distribution of light emitted by the lighting device. In some embodiments the lighting device also comprises a clock and a programmable user interface for programming the lighting device to vary the light output both in color and intensity during user selected time intervals.

Embodiments of the invention include a lighting device that provides adjustable spectral and spatial illumination to facilitate or coordinate with human circadian rhythms and comprises a first illumination source comprising an LED of a first color temperature that is rich in melanopic light, a second illumination source comprising an LED of a second color temperature that is depleted in melanopic light, and a light distribution unit for directing and distributing illumination generated by the first and second illumination sources wherein at least one of said first illumination source and said second illumination source is proximal to said light distribution unit and wherein the first and second illumination sources are oriented relative to one another such that their respective light outputs are directed in different directions.

In some embodiments, the respective light outputs of the first illumination source and the second illumination source are generally in opposite or near-opposite directions, and in some embodiments of the lighting device, the light output from the first illumination source is generally directed upward and away from a floor or lower portion of a room or other space and results in indirect lighting from above and the light output from the second illumination source is generally directed downward towards a floor or lower portion of a room or other space. In some embodiments, the lighting device includes a light distribution unit capable of being edge-lit and wherein the first color temperature is greater than about 4000 K and the second color temperature is less than about 2700 K. In some embodiments a first light source generates illumination of relatively high equivalent melanopic lux or with high melanopic ratio and a second light source generates illumination with a relatively low equivalent melanopic lux or with a low melanopic ratio. In some embodiments, the lighting device comprises means for independently adjusting the illumination output of both the LED of the first color temperature and the LED of the second color temperature whereby the lighting device can be configured such that its illumination output comprises relatively high melanopic flux during the daytime and relatively low melanopic flux at nighttime.

Embodiments of the invention also include a lighting fixture with integrated functions operable to deliver adjustable spectral and spatial illumination comprising a base, an edge lit shade above and attached to said base, a first illumination source comprising a set of LEDs of a first color temperature affixed to a lower portion or edge of the edge lit shade wherein said set of LEDs of the first color temperature are oriented to produce illumination generally upward and away from said base, a second illumination source comprising a set of LEDs of a second color temperature affixed to an upper portion or edge of the edge lit shade wherein said set of LEDs of the second color temperature are oriented to produce illumination generally downward in the direction of said base, a speaker for generating acoustic waves, and a programmable interface integrated into said base for programming or operating the lighting device and whereby the intensity of illumination output of both the first set of LEDs and second set of LEDs may be adjusted.

Embodiments of the invention include a lighting fixture in the form of a table or floor lamp, and wherein a first illumination source comprises daytime LEDs rich in melanopic light and a second illumination source comprises nighttime LED depleted in melanopic light. Other embodiments of the lighting fixture include a clock and automatic illumination adjustment feature that automatically varies the outputs of daytime LEDs and nighttime LEDs depending on the time of day in order to facilitate, regulate or prevent interference with natural circadian rhythms. Some embodiments include a lighting fixture with an edge-lit shade that is adjustable such that the illumination output of the lighting fixture may be spatially varied and redirected. Some embodiments include a lighting fixture with integrated and programmable sleep and wake functions that combine both dynamic sound and light variation and output to facilitate falling asleep or waking up respectively. Some embodiments include a pendant luminaire that provides both indirect lighting of high melanopic ratio and direct lighting (e.g., task lighting) of low melanopic ratio. Other embodiments include a troffer type luminaire or fixture that provides both illuminations of high melanopic ratio and of low melanopic ratio, each respective illumination occupying a different spatial distribution.

BRIEF DESCRIPTION OF THE DRAWINGS

FIGS. 1a-c illustrate lighting devices for providing spectrally and spatially adjustable illumination according to some embodiments.

FIGS. 2a-c illustrate the structure and configuration of a light distribution unit and associated LEDs according to some embodiments.

DETAILED DESCRIPTION

Figure 1A:
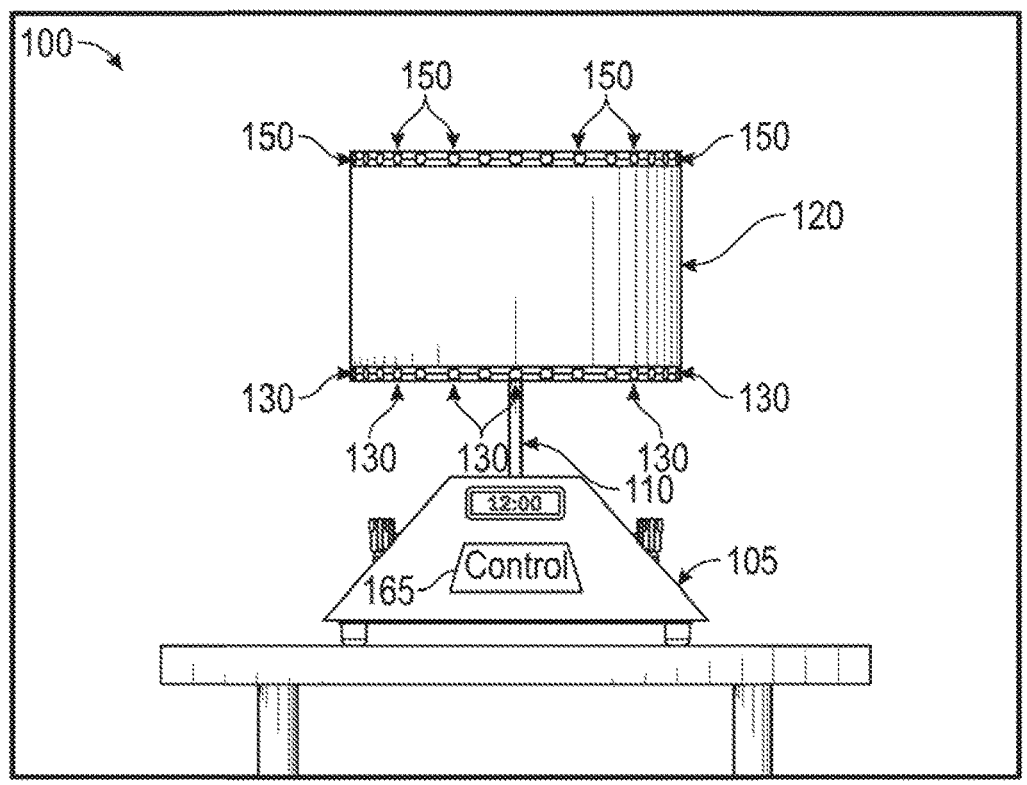

Embodiments of the invention include methods, systems and luminaires that dynamically generate high efficacy white light that comprises enhanced spectral components that can vary in aspects of spectral and spatial distribution as well as intensity at different times of the day to facilitate circadian regulation or entrainment. Embodiments of the invention include dynamic illumination methods and systems for providing relatively high melanopic flux during the day and relatively low melanopic flux at night. Other embodiments of the invention include lighting systems which provide indirect illumination from the upper portions of the visual field of an observer wherein such illumination is enriched in melanopic light. In some embodiments, the exposure of melanopic light to photoreceptors in the lower hemisphere of the retina may be amplified or attenuated based on time of day in order to facilitate circadian rhythm regulation. Some embodiments include a lighting fixture which provides task lighting and/or indirect illumination from the lower portions of the visual field of an observer that is depleted in melanopic light. Some embodiments include luminaires or lighting fixtures which provide both indirect lighting from the upper portions of visual fields rich in melanopic light and task lighting and indirect lighting from the lower portions of visual fields that are depleted in melanopic light. In some embodiments, a lighting fixture in the form of a table lamp comprises two of more different sources of illumination, differing in their respective output spectrums, and for which the spectral outputs (e.g., amount of melanopic light), the spatial distributions of said illuminations and the relative intensities of the illuminations may be varied. In some embodiments, the spectral, spatial and intensity variations may be coordinated with the local time or user preference to facilitate the coordination of human circadian rhythms or other biological effects.

Embodiments of the invention include methods, luminaires and systems for providing biologically relevant light (e.g., melanopic light) from indirect illuminating sources and from sources which direct various spectral types of light in specific spatial directions and illuminate specific areas. When used herein, the term day-time LEDs may be used and is meant to refer to LEDs that produce illumination rich in melanopic light or which have a relatively high melanopic ratio and which generate relatively high equivalent melanopic lux. Similarly, the term night-time LEDs means LEDs that produce illumination that is relatively low or depleted of melanopic light or which have a relatively low melanopic ratio and which generate relatively low equivalent melanopic lux. Embodiments include desk and floor lamps which comprise covers or shades which are edge-lit and comprise different types of LEDs, one set of LEDs producing light which is depleted of melanopic light and another set which produces light rich in melanopic light illuminated. In some embodiments, the biological effective LEDs (those that provide illumination rich in melanopic light) are configured in or in relation to the edge-lit shade such that the illumination provided by those LEDs project upward (i.e., up and outward toward the ceiling and the walls surfaces generally at or above eye level). In some embodiments, the LEDs which are depleted in melanopic light are configured in or in relation to the edge-lit shade such that the illumination from the melanopic-depleted LEDs is projected downward (i.e., toward the floor/desk and outward generally below eye level). In some embodiments, the desk/floor lamp comprises a selective dimmer which allows one or both of the different types of LEDs to be dimmed such that the intensity of the respective illuminations may be adjusted (e.g., the intensity of illumination produced by the daytime and/or nighttime LED may be adjusted). In some embodiments, such dimming may be automatic and may be programmed and/or coordinated with the time of day or user preference. Embodiments also include various configurations of light distribution units for reflecting and/or transmitting and generally directing light spatially.

In one embodiment, a desk lamp that comprises a "shade" comprised of light-transmissive guide material is configured such that daytime LEDs illuminate the shade from below, resulting in an edge-lit shade that projects the daytime illumination upwards and outwards, and nighttime LEDs illuminate the shade from above resulting in nighttime illumination projecting downwards and outwards. The daytime light (rich in melanopic light) is projected onto the ceiling and upper portions of surrounding walls or partitions, and is reflected therefrom. This reflected indirect light from above may disproportionately impinge on the lower hemisphere of the retina of a conventionally oriented observer in the lighted space. This type of daytime light spatial distribution may be appropriate for optimal melanopic photoreceptor stimulation because the lower hemisphere of the retina is most sensitive to melanopic light relative to the upper hemisphere. Additionally, illumination from the night time LEDs is projected downward onto the task areas, e.g., a desk. During periods of the day when it would be inappropriate to receive melanopic light (for instance late in the day prior to bedtime), the nighttime LEDs will provide good illumination for task work, but will not be rich in melanopic light and therefore will have no or little impact or disruption the circadian rhythm of the individual(s) exposed to the illumination.

Transparent and translucent materials may be used for portions of the light distribution unit (e.g., shade, diffuser, etc.) An example of such material is acrylic. Edge-lit technology is well known and readily available in the lighting industry. Materials for use in embodiments of the invention may be obtained from a number of sources including the firm ACRYLITE. Light guides and other types of edge-lit technologies and materials may be employed in embodiments of the invention. For instance, clear shade acrylic may be used and shaped such that light from one set of LEDs illuminating the acrylic from the bottom edge will be transmitted upwards through the acrylic and outwards from the acrylic to provide the edge-lit effect. Similarly, light from another set of LEDs illuminating the acrylic from the top edge will be transmitted downwards through the acrylic and outwards from the acrylic to provide the edge-lit effect. Holographic diffuser can also be used to provide desired or optimal light distribution. Embodiments of the invention are not limited to any specific material, and a variety of materials and combinations thereof, including transparent, translucent, reflective, opaque, etc., may be used to achieve spectral, spatial, and intensity variations of illuminations are contemplated by embodiments of the invention.

In some embodiments, a desk or table lamp may comprise a programmable interface and clock to coordinate the illumination output (spectral, spatial, and/or relative intensity) with the time of day and users schedule, and/or such that the user can input specific idiosyncratic parameters or desires in order to adjust and optimize the illumination of the luminaire, e.g., throughout the day, to match a users schedule, and to facilitate regulation of the individuals circadian rhythm, sleep cycles and period of acute alertness. Examples of such inputs include but are not limited to users desired sleep/wake schedules, desired light color and intensity depending on activity, subjective feelings of sleep quality, desire to shift sleep schedule et cetera.

In some embodiments the desk lamp also comprises a sound system capable of producing and projecting music or other sounds such as white or pink noise, bedtime beats, relaxation sounds, etc. In some embodiments, the light from the lamp may be modulated in coordination with the music to produce a show. In some embodiments the sound may be dynamically coordinated with the light to help the individual sleep or wake or concentrate. In some embodiments, the luminaire can dynamically adjust the spectrum (and/or sounds) throughout the day, for instance in the form of a dawn to dusk light show. Additional lighting features according to some embodiments include: a party mode (color, animation, music synchronization etc); jet-lag fighter (e.g., pre-travel shift and post-travel shift); circadian optimizer; calming feature (e.g., beat synch, synch with heart beat or respiration); directional nightlight (e.g., singular facade); Nighttime light sensor (e.g. send text when lamp senses presence of bright or blue light).

Figure 1B:
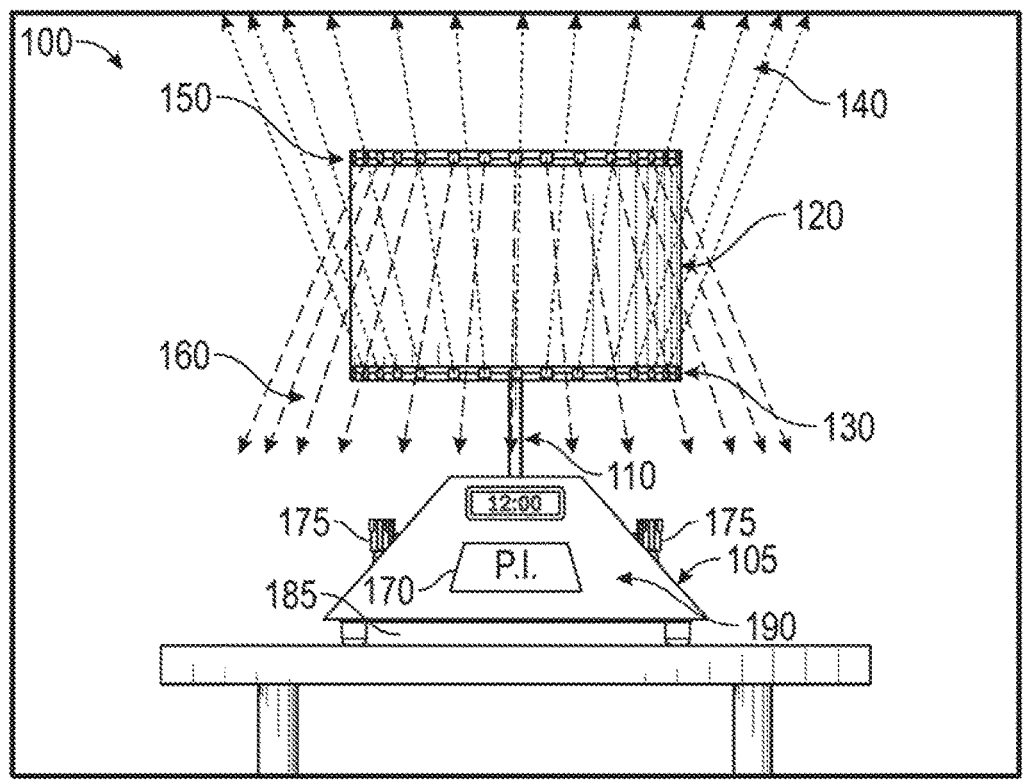

FIGS. 1a-c illustrate embodiments of the invention. FIG. 1a shows a desk or table lamp 100 that comprises a base 105, a lamp shade holder 110, a light distribution unit in the form of an edge-lit lampshade 120 (other forms of shades, reflectors, diffusers, etc. may also be used as will be evident to those skilled in the art), daytime LEDs 130, nighttime LEDs 150, and a control interface 165. The daytime LEDs 130 are attached to the underside or lower portion of the lampshade 120 or otherwise integrated therein and are oriented such that light emitted from them is generally upward, for example the opaque non-emitting portion of the LED die or package is oriented facing toward the base 105. The nighttime LEDs 150 are attached to the upper side or upper portion of the lampshade 120 or otherwise integrated therein and are oriented such that light emitted from them is generally downward, for example the opaque non-emitting portion of the LED die or package is facing away the base 105. The control interface 165 may comprise one or more toggle switches for turning the daytime and nighttime LEDs on and off. The control interface 165 may also comprise a dimming control for adjusting the intensity of the daytime LEDs, the nighttime LEDs or both. An optional clock 180 is also shown. Desk or table lamp 100 also includes a power source (not shown). In alternative embodiments, the light distribution unit or lamp shade 120 is not edge lit and may be designed with various degrees of relative transparency to allow various patterns of illumination (e.g., a uniform cone-like distribution or alternatively a greater degree of the illumination directed in the vertical direction with a less transparent shade). In some embodiments the daytime LEDs provide illumination with a melanopic ratio of greater than 0.8. In other embodiments the melanopic ratio is greater than 1.0. In still other embodiments, the MR is greater than 1.2. In some embodiments the nighttime LEDs provide illumination with a melanopic ratio of less than 0.8. In other embodiments the melanopic ratio is less than 0.6. In still other embodiments, the MR is less than 0.4.

The configuration of the daytime LEDs 130 and Lamp Shade 120 and the control interface 165 provide for the projection and control (e.g., dimming) of melanopic rich light illumination upward such that, for example, more melanopic rich light would be more likely to fall on the lower hemisphere of a person's retina who is in proximity to the lamp and surrounding surfaces. The configuration of the nighttime LEDs 150 and Lamp Shade 120 and the control interface 165 provide for the projection and control (e.g., dimming) of light that is depleted in melanopic light downward such that, for example, when an individual is working on a task, e.g., on a desk or table surface, the individuals retina is not exposed to significant amounts of melanopic rich light, light which may not be appropriate at a particular time of day for a particular individual. These configurations allow for an individual to receive the needed melanopic light during the day while being able to avoid melanopic light during periods where it may interfere or disrupt the person's circadian rhythms or sleep patterns. The intensity of the daytime and nighttime LEDs may be varied using the control interface 165.

FIG. 1b illustrates another embodiment of the invention. Desk or table lamp 100 comprises a base 105 a lamp shade holder 110, a light distribution unit in the form a lamp shade 120, daytime LEDs 130, nighttime LEDs 150, and programmable interface (PI) 170. The programmable interface 170 comprises means for both manual and automatic control of the lighting device features including lighting intensity, color and spatial distribution as well as other features described further below. Also shown schematically (although not to scale and not meant to represent the actual illumination pattern but shown for illustrative purposes) are representations of the Upward Projection 140 of the illumination from the Daytime LEDs 130 and the Downward Projection 160 of the illumination from the Nighttime LEDs 150.

Table lamp 100 also comprises a sound system (not fully shown integrated in said base) including a woofer or other speaker means 175, a clock 180, a means for wireless communications (not shown) and may additionally include various optional sensors (not shown) including an ambient light sensor. The programmable user interface 170 is used for accessing and/or programming these elements. As can be seen from the Figures, the base may be so designed as to optimize acoustics. For instance an offset of the base from the table surface provides a resonant air gap offset 185 and a cover 190 may be shaped and configured for sound consolidation and other acoustical performance. In some embodiments the sound system and illumination output may be coordinated to produce a number of desired features as mentioned elsewhere herein.

The lighting fixture 100 comprises a power source not shown. Delivering and regulating electrical power to the components of the desk lamp are well known to those skilled in the art. Examples of power sources are switched mode power supplies and other power supplies that can supply and adjust current and voltage supplied to the LEDs and/or LED light engines, the processing hardware (e.g., circuit board, memory and CPU) and sound system including woofers etc. In some embodiments the power source is wall AC supplied by a conventional pronged plug (not shown).

FIG. 1c shows a perspective view of a spectrally and spatially tunable lighting device according to some embodiments. According to some embodiments, the lighting fixture 100 also may also comprise additional activation and/or control interfaces, e.g., manuals switches, dimmers, and means to adjust the orientation of the light distribution unit or shade to spatially direct the light. In some embodiments, the shades transparency may be adjusted (via structural means or electro-optic means) to alter the spatial, spectral and/or intensity distribution of the illumination from the lighting fixture 100. The interfaces may be analog, digital or both. In some embodiments, the desk lamp is configured to operate with wireless communications and be capable of receiving programming instructions or actual commands (e.g., on/off, dimming, etc), and transmit data, (e.g., status, user input, etc). The user interface may comprise a digital display for entering inputs. Alternatively a networked interface may allow the user to control and/or program the operation of the desk lamp remotely (e.g., via computer or smart phone). In some embodiments, the desk lamp comprises a programmable microcontroller that allows for fine control over the spectral and spatial illumination output including intensity control. Additional embodiments include programmed light shows throughout the day, coordination with sounds or music from the sound system, and recording and tracking a users habits or preferences and real-time dynamic illumination adjustment capability to facilitate regulation of circadian rhythms, aesthetics and other effects. In some embodiments, the lamp shade is clear or transparent. In some embodiments the portion of the desk lamp interior of the lampshade is empty.

FIGS. 2a-c illustrate a light distribution device 120 according to some embodiments of the invention. FIG. 2a shows a perspective view and FIGS. 2b and 2c show top and side views respectively of the light distribution device 120. Light distribution device 120 comprises generally a hollow cylinder that comprises transparent or translucent material. In some embodiments, the material is capable of being edge lit. In these embodiments, daytime LEDS 130 are affixed to a lower portion of the device 120 and oriented such that their light emitting surfaces are facing upwards, and the nighttime LEDS 150 are affixed to an upper portion of the device 120 and oriented such that their light emitting surfaces are facing downwards.

Although the light distribution device is shown as a cylindrical shape with a hollow central structure, embodiments of the invention are not limited to particular shapes, fills, or materials, and many different shapes materials and orientations of light distribution devices 120 are contemplated by the invention. Additionally, although the daytime LEDs 130 and nighttime LEDs 150 are shown as placed around the lower and upper peripheries respectively of the light distribution device 120 and are generally oriented in a vertical facing direction (i.e., up or down), the invention is not limited to any specific placement of LEDs on the light distribution device 120 or specific orientations thereof. As will be evident to those skilled in the art, a variety of configurations, placements and orientations of the light distribution device 120 and the LEDs 130 and 150 may be utilized to achieve the desired spectral and spatial illuminations and adjustments thereof, for example, daytime light directed generally upward and/or resulting in indirect illumination from above and nighttime light directed generally downward providing both task lighting and indirect lighting from below.

Figure 3A:
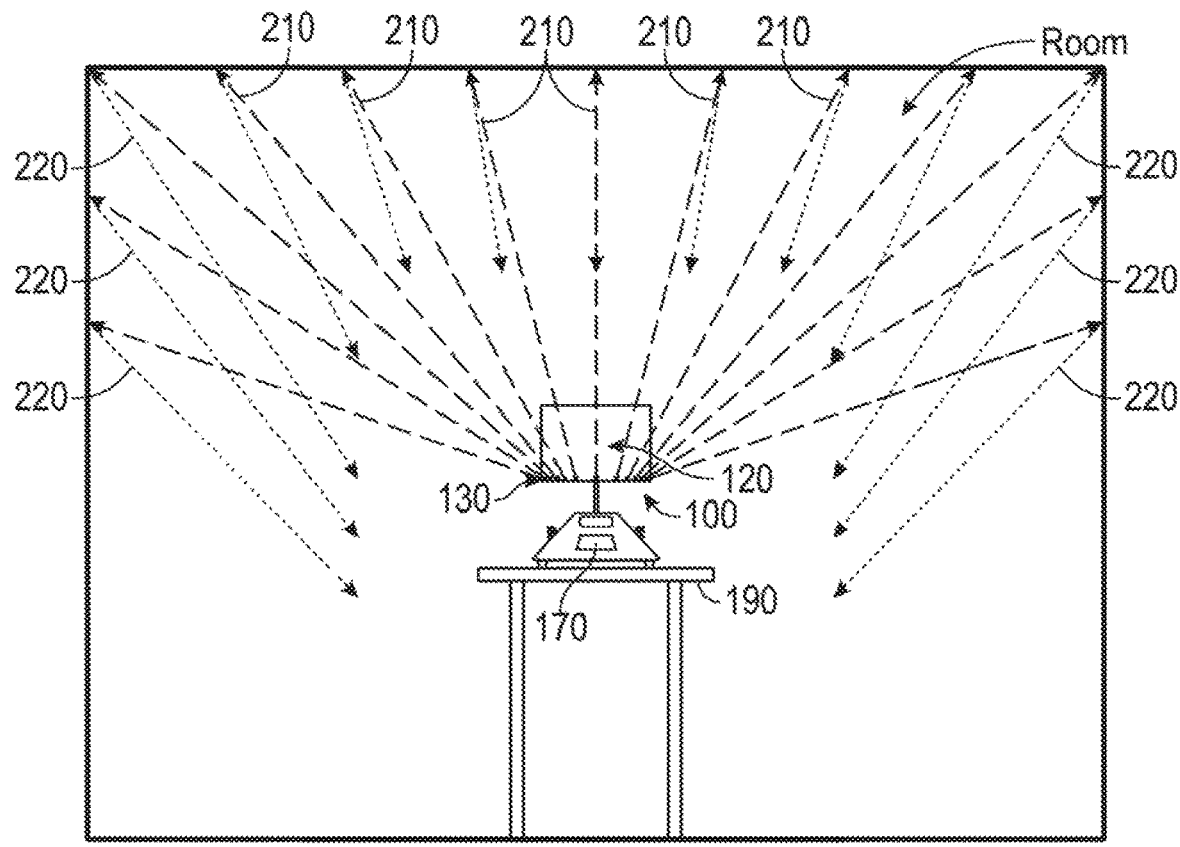
FIGS. 3a and 3b illustrate spatial illumination patterns of a lighting device in accordance with embodiments of the invention.
Figure 3B:
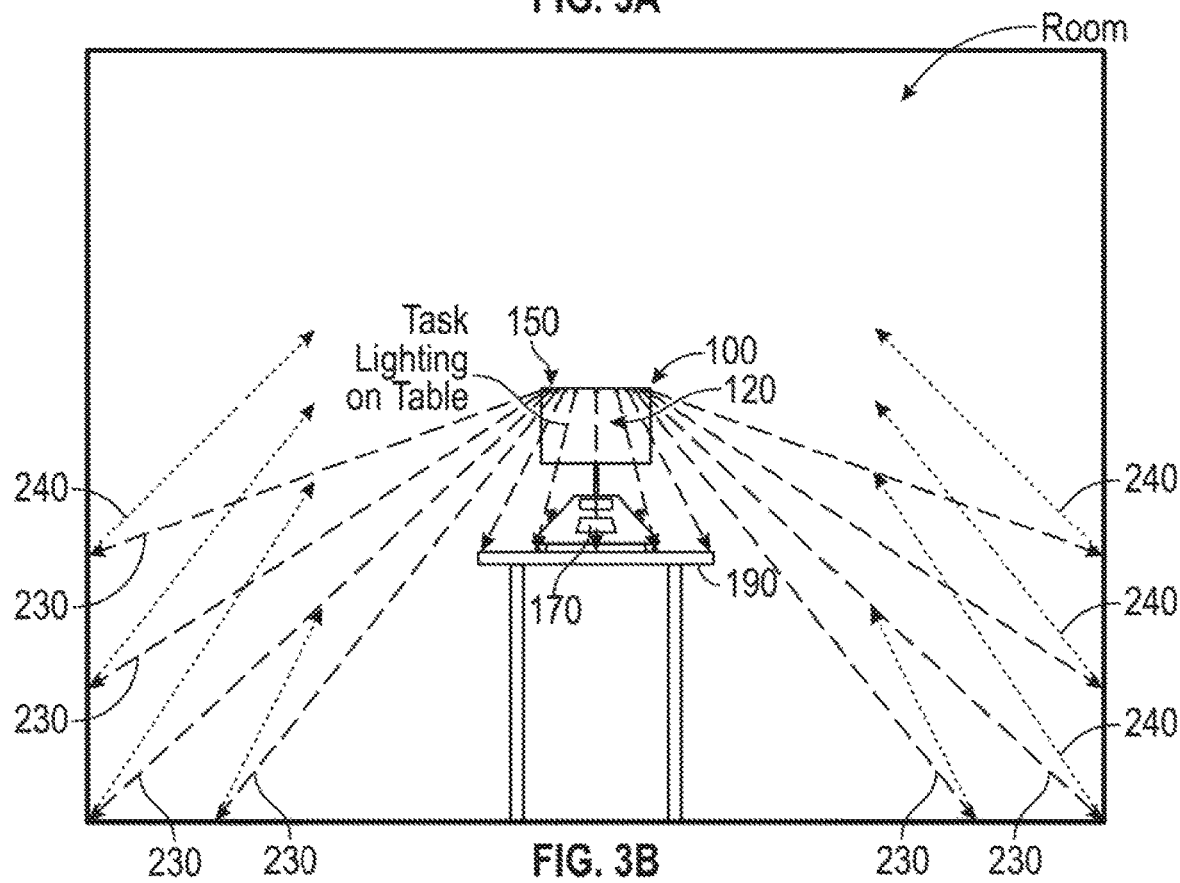

FIGS. 3a and 3b show schematically and generally light distribution patterns of a table lamp 100 on table or platform 190 comprising both daytime LEDs 130 and nighttime LEDs 150 according to some embodiments. FIG. 3a shows the light distribution pattern of the lighting fixture 100 due to the daytime LEDs 130 when they are powered to illumination. Emitted light 210 is generally upwardly directed and results in reflected indirect light 220 that is generally downwardly directed. Daytime LEDs will generate illumination of higher melanopic ratio than nighttime LEDs.

FIG. 3b shows the light distribution pattern of the lighting fixture 100 due to the nighttime LEDs 150 when they are powered to illumination. Emitted light 230 is generally downwardly directed and results in both task lighting on the table 190 and reflected indirect light 240 that is generally upwardly directed. Control interface 170 provide means to inter alia turn the daytime LEDs 130 and nighttime LEDs 150 on or off and adjust their respective intensities.

The light distribution patterns shown in the figures are for illustration purposes only and, as will be evident to those skilled in the art, do not represent actual illumination patterns. The patterns shown are meant to illustrate how light from the daytime LEDs 130, which is upwardly directed, reflects off of the ceiling and the upper portions of walls resulting in indirect lighting directed downward to an observer in the room, and thereby disproportionately impinges on the lower hemisphere of the observer's retina as compared to upper hemisphere of the retina. Similarly, the illumination from the nighttime LEDs 150 results in direct task lighting on the desk or table top and otherwise reflects from the floor or lower portions of the walls resulting in indirect light directed generally upward to an observer in the room, and thereby may disproportionately impinge on the upper hemisphere of the observer's retina as compared to lower hemisphere of the retina.

In some embodiments, the lighting fixture, e.g., in the form of a table or desk lamp, may be optimized for bedroom or sleep use generally and may include a dynamic light controller that may be programmable and that comprises sensors and/or a receiver for data input and actuators to output sound, illumination or other output signals and/or data. The lighting fixture may include means for wireless communication including WiFi, Bluetooth or other communication protocols. This communication capability allows for a user to access, read and program the lighting device remotely and allows for the lighting device to read or sense ambient data and communication information externally and control local or remote devices.

In some embodiments, the lighting device may include any or all of the following: thermometer for measuring ambient temperature, humidity sensor, an ambient light sensor, a bed occupancy sensor, a proximity sensor, geo-location sensor, a speaker for outputting music, speech or other sounds, and a microphone for recording or to receive spoken commands. In some embodiments the proximity and/or bed occupancy sensor may be used to determine which lighting levels to provide via the lighting device to optimize the experience of the user or occupant. In some embodiments, the lighting device comprises a user display that may include inter alia a clock, sensor status, wireless communication status, battery level, etc.

The bedroom lighting fixture according to some embodiments has the capability to provide both spectrally tunable light as well as spatially variable light and may be programmed to facilitate both falling asleep and waking up. For example, as an occupant approaches sleep time, light with low melanopic impact may be used instead of light with a higher melanopic effect and may be spatially directed, at for example the floor, to minimize any alerting effect or sub-optimal impact on the occupant's circadian rhythm. Conversely, during a wake up period or when the occupant wishes to remain awake or alert, melanopic light may be generated by the lighting device to suppress or mitigate sleep pressure and/or shift of otherwise effect the circadian rhythm of the occupant. In some embodiments, music or other sounds generated by the lighting device sound system accompanies and is coordinated with the illumination provided thereof to facilitate sleeping or waking. The lighting device may be powered by an AC-DC power supply and may use various voltage and current regulation schemes to optimize efficiency and performance. The lighting device may also include a battery for backup power.

While the invention has been described with reference to exemplary embodiments, it will be understood by those skilled in the art that various changes may be made and equivalents may be substituted for elements thereof without departing from the scope of the invention. It should be understood that the diagrams herein illustrates some of the system components and connections between them and does not reflect specific structural relationships between components, and is not intended to illustrate every element of the overall system, but to provide illustration of the embodiment of the invention to those skilled in the art. Moreover, the illustration of a specific number of elements, such as LED drivers power supplies or LED fixtures is in no way limiting and the inventive concepts shown may be applied to a single LED driver or as many as desired as will be evident to one skilled in the art.

In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include many variants and embodiments. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A lighting device that provides adjustable spectral and spatial illumination to facilitate or coordinate with human circadian rhythms comprising:
    a first illumination source comprising a light-emitting diode (LED) of a first color that generates a first light output with a first melanopic ratio of 0.4 to 1.2;
    a second illumination source comprising an LED of a second color that generates a second light output with a second melanopic ratio that is less than the first melanopic ratio;
    a light distribution unit for directing and distributing illumination generated by the first and second illumination sources, wherein at least one of the first illumination source and the second illumination source is affixed to the light distribution unit, and wherein the first and second illumination sources are oriented relative to one another such that their respective light outputs are directed in different directions.

2. The lighting device of claim 1 wherein the first light output of the first illumination source and the second light output of the second illumination source are generally directed in opposite directions.

3. The lighting device of claim 1 wherein the first light output from the first illumination source is generally directed upward and away from a floor or lower portion of a room or other space and results in indirect lighting from above, and wherein the second light output from the second illumination source is generally directed downward towards the floor or lower portion of the room or other space.

4. The lighting device of claim 1 wherein the light distribution unit is edge-lit by the first illumination source and the second illumination source.

5. The lighting device of claim 1 wherein the first melanopic ratio of the first illumination source is greater than about 1.0, and the second melanopic ratio of the second illumination source is less than about 1.0.

6. The lighting device of claim 1 wherein the first melanopic ratio of the first illumination source is greater than about 0.5 and the second melanopic ratio of the second illumination source has a melanopic ratio of less than about 0.5.

7. The lighting device of claim 1 wherein:
the first illumination source is affixed to a lower portion of the light distribution unit, with the first light output oriented in an upward direction; and
the second illumination source is affixed to an upper portion of the light distribution unit, with the second light output oriented in a downward direction.

8. The lighting device of claim 1 wherein the first color has a color temperature greater than 4000 K and the second color has a color temperature less than 2700 K.

9. The lighting device of claim 1 wherein the light distribution unit is a shade or diffuser.

10. The lighting device of claim 1 further comprising a control interface that varies spectral intensities of the first light output and the second light output.

11. The lighting device of claim 1 further comprising a control interface for independently adjusting the first light output of the LED of the first color and the second light output of the LED of the second color, and whereby the lighting device outputs a melanopic flux during daytime that is higher than at nighttime.

12. The lighting device of claim 1 further comprising a control interface that varies a spatial direction, orientation and distribution of the first light output and the second light output emitted by the lighting device.

13. The lighting device of claim 1 further comprising a networked interface allowing a user to remotely operate the lighting device.

14. The lighting device of claim 1 further comprising a programmable light controller that controls the first illumination source and the second illumination source.

15. The lighting device of claim 14 wherein the programmable light controller further comprises a sensor or a receiver for data input.

* * * * *